US005485828A

United States Patent [19]

Hauser

[11] Patent Number: 5,485,828

[45] Date of Patent: Jan. 23, 1996

[54] PORTABLE DEVICE FOR MICROPULVERIZATION GENERATED BY ULTRASOUND WAVES

[76] Inventor: Jean-Luc Hauser, 1499 chemin S. Maymes, F-06600 Antibes, France

[21] Appl. No.: 170,221

[22] PCT Filed: Apr. 28, 1993

[86] PCT No.: PCT/FR93/00411

§ 371 Date: Dec. 28, 1993

§ 102(e) Date: Dec. 28, 1993

[87] PCT Pub. No.: WO93/22068

PCT Pub. Date: Nov. 11, 1993

[30] Foreign Application Priority Data

Apr. 29, 1992 [FR] France .................................. 92 05306

[51] Int. Cl.⁶ .................................................. A61M 11/00

[52] U.S. Cl. ............................... 128/200.16; 128/200.21; 128/203.12; 239/102.2

[58] Field of Search ......................... 128/200.16, 200.18, 128/200.21, 203.12, 200.22, 200.23; 239/102.2

[56] References Cited

U.S. PATENT DOCUMENTS

| | | | |
|---|---|---|---|
| 3,321,189 | 5/1967 | Scarpa . | |
| 3,387,607 | 6/1968 | Gauthier et al. | 128/200.16 |
| 3,433,461 | 3/1969 | Scarpa . | |
| 3,561,444 | 2/1971 | Boucher | 128/200.16 |
| 3,828,773 | 8/1974 | Buch et al. | 239/102.2 |
| 4,094,317 | 6/1978 | Wasnich | 128/200.16 |
| 4,300,546 | 11/1981 | Kruber | 239/102.2 |
| 4,976,259 | 12/1990 | Higson et al. | 128/200.18 |
| 5,152,457 | 10/1992 | Burwell et al. | 239/102.2 |

FOREIGN PATENT DOCUMENTS

| | | | |
|---|---|---|---|
| 2655279 | 6/1991 | France . | |
| 2690510 | 10/1993 | France | 128/200.16 |
| 22150 | 10/1961 | German Dem. Rep. | 128/200.16 |
| 1003147 | 2/1957 | Germany | 128/200.16 |
| 26041 | 11/1963 | Germany | 239/102.2 |
| 3225951 | 1/1984 | Germany | 239/102.2 |
| 114812 | 9/1979 | Japan | 239/102.2 |
| 5123400 | 5/1993 | Japan | 128/200.16 |

OTHER PUBLICATIONS

Ultrasonic Oscillator; Patent Abstracts of Japan; vol. 10, No. 136 (C-347); p. 131; Heitarou Segawa.

*Primary Examiner*—Edgar S. Burr
*Assistant Examiner*—William J. Deane, Jr.
*Attorney, Agent, or Firm*—Francis A. Sirr; Earl C. Hancock

[57] ABSTRACT

An acoustic micropulverization device for the formation of microdroplets is disclosed having a cell that contains a propagating medium having an attenuation less than or equal to about 1 dB/cm. One wall of the cell comprises an ultrasonic generator. Another wall of the cell contains a reflective surface that operates to focus ultrasonic waves upward toward a point that is near the top surface of a liquid that is contained in a reservoir located above the cell, thereby producing microdroplets above the liquid's top surface. A chamber is located over the top surface of the liquid. This chamber includes means for diffusing the microdroplets.

8 Claims, 1 Drawing Sheet

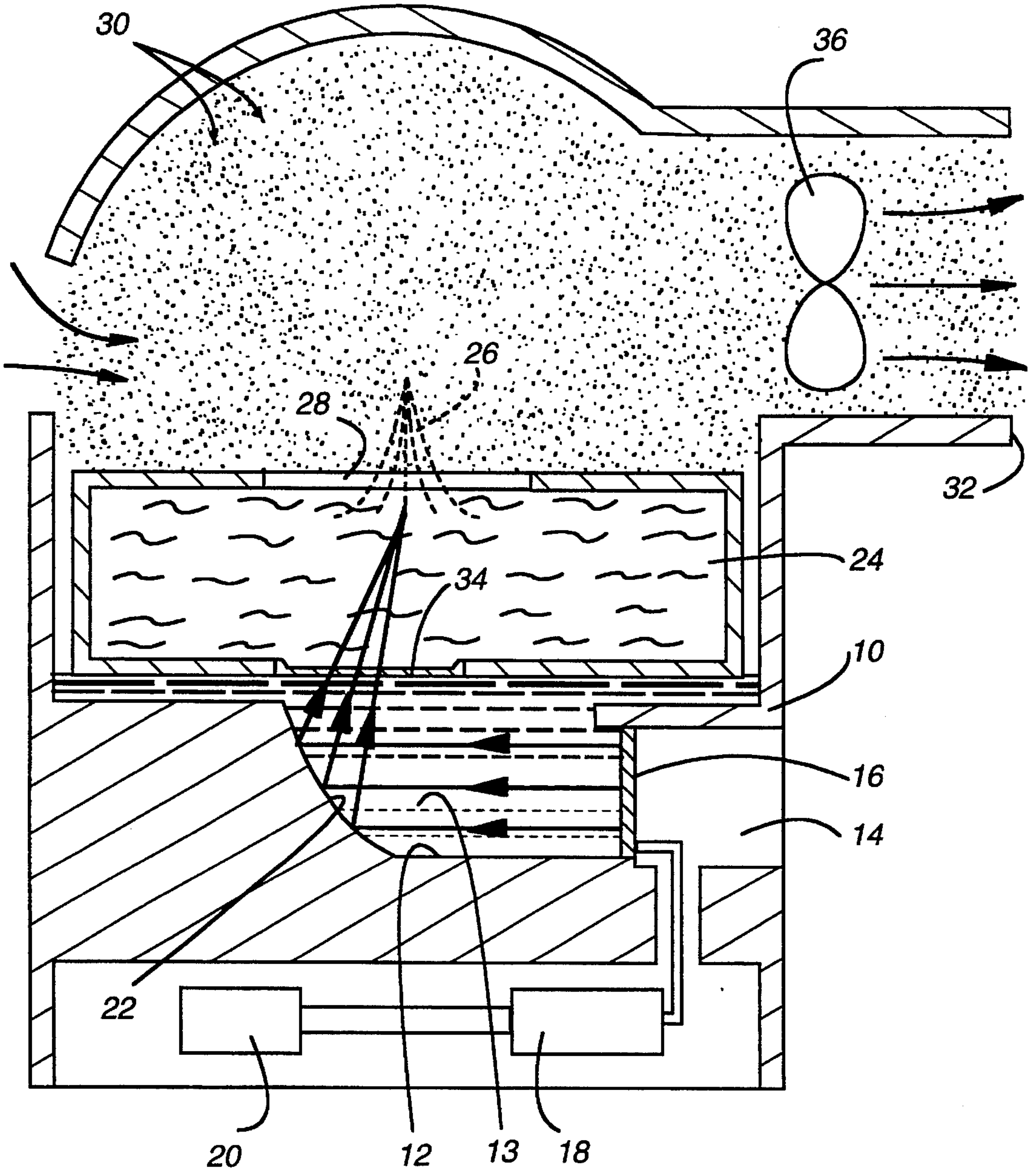
30
36
26
28
32
24
34
10
16
14
22
20
12
13
18

PORTABLE DEVICE FOR MICROPULVERIZATION GENERATED BY ULTRASOUND WAVES

BACKGROUND OF THE INVENTION

1. Field of the Invention

This invention concerns a micropulverization device of a type including an ultrasound wave generator, a means for focusing ultrasound waves at one point at least in the liquid for micropulverization near its surface, a chamber for the formation of microdroplets and a means for diffusing the microdroplets thus formed.

2. Description of Prior Art

Conventional therapy makes considerable use of pulverization devices when it is necessary to apply microdroplets to the part of the body to be treated, usually an internal part, such as the nose, throat or bronchi.

Conventional pulverization devices based on mechanical pulverization, such as vaporizers with a nozzle under pressure or piezoelectric sprays using a cone do not make it possible to obtain microdroplets of sufficiently small diameter to be effective for some therapy. Thus, for pneumological applications, it is necessary to generate aerosols in microdroplets.

For several years, the ultrasound pulverizing technique has been used to generate a mist of microdroplets. In this technique, ultrasound waves are generated using electromechanical transducers in a liquid bath. The ultrasound wave beam is directed towards the surface of the bath where the water-air impedance interruption creates a liquid jet called 'acoustic fountain'. This phenomenon is accompanied by a mist of microdroplets between 3 and 6 μm in size, created by cavitation or by resonance of the jet's capillary waves.

The above technique is applied in patent FR-89/16.424 describing a process and device for micropulverization of a liquid solution using ultrasound to obtain microdroplets to form a mist of disinfectant products for asepsis on medical premises. But devices of the type described in the above patent have the disadvantage of requiring a large amount of liquid for micropulverization, since the ultrasound waves are transmitted inside the liquid. Because of the considerable amount of liquid for micropulverization, it is necessary to foresee a system for preheating the liquid. Devices of this type are thus generally bulky, wasteful and require a great deal of care in their use (assay, sterilization, cleaning, heating temperature . . . ).

This disadvantage has been partially reduced by focusing ultrasound waves in a propagation medium different from the liquid for micropulverization. Thus, in patent DE-B-1.003.147, focusing is performed by concentrating the waves using a circular wave generator, in which the centre coincides with the point where micropulverization is to take place.

Another type of focusing involves using a system for concentrating ultrasound waves using a Fresnel-type lens as described in U.S. Pat. No. A-3.433.461.

All these systems use the non-linearity of the ultrasound wave field to obtain good pulverization at the focusing point. The distribution of energy between the fundamental frequency (generator exciting frequency), upper harmonics and subharmonics varies with propagation distance in the propagation medium. There should thus be a minimum propagation distance for ultrasound waves to obtain the greatest possible efficacy at the focusing point.

Consequently, the systems described in the abovementioned patents have the disadvantage of being bulky and are not intended for use as portable equipment.

Moreover, a great amount of energy is required for generating ultrasound waves since there must be a relatively powerful source of ultrasound waves to obtain sufficient energy at the wave focusing point after considerable attenuation, either by the propagation liquid as in patent DE-B-1, 003.147, or through the Fresnel lens as in U.S. Pat. No. A-3,433,461. This is why the devices described are connected to an outside source and no autonomous energy source is foreseen to make them portable.

SUMMARY OF THE INVENTION

This invention thus aims at eliminating these disadvantages through a small, efficient micropulverization device, requiring no preheating.

Another purpose of the invention is to supply a micropulverization device using ultrasound waves in which attenuation of the waves is reduced to a minimum.

Yet another purpose of the invention is to supply a micropulverization device as described above, with its own energy supply, making it portable.

The invention is a micropulverization device of 'acoustic-fountain' type in which the means of focusing ultrasound waves at one point at least in the liquid for micropulverization and close to its surface is a medium for propagating ultrasound waves without significant attenuation and the liquid for micropulverization is in a reservoir separate from the one containing the propagation medium.

BRIEF DESCRIPTION OF THE DRAWING

The FIGURE shows an acoustic fountain type micropulverization device in accordance with the invention.

DESCRIPTION OF THE PREFERRED EMBODIMENTS

The invention will be better understood after reading the following description, which makes reference to the figure showing the preferred form of the micropulverization device according to the invention.

As illustrated in the figure, the micropulverization device according to the invention includes a package 10 with a cell 12 containing propagation medium 13 for ultrasound waves without significant attenuation. Cavity 14 is closed by an electromechanical transducer 16, such as a piezoelectric transducer. Transducer 16 is supplied with a frequency between 1 and 5 megahertz by an electronic circuit 18 running on batteries 20. The transducer then generates ultrasound waves in cell 12. These waves shown by arrows in the figure are focused by an appropriate reflecting surface 22, of paraboloid or parabolic cylinder type. The ultrasound waves are sent through a cassette 24 containing the liquid for micropulverization to concentrate at one point in the liquid near its surface. A jet-shaped 'acoustic fountain' 26 thus forms on the surface of the liquid for micropulverization above the opening 28 of cassette 24. This jet 26 generates a mist of relatively uniform microdroplets 30 with the smallest diameter between 3 and 6 μm. The mist is moved towards the inhaler or diffuser 32 by ventilator 36.

Although here the reflecting surface 22 is of parabolic type, it is possible to optimize the form of this surface by digitally resolving the integral radiation equations associated with the wave equation, although the frequencies used (fundamental and harmonics) are not high enough to use radiation theory (wavelengths too high compared to the bending radius).

The medium 13 for propagating ultrasound waves must be a fluid of low density close to 1 to obtain proper celerity of acoustic waves, and so as not to add weight to the device. This medium must have a high non-linearity ratio for the greatest possible efficiency at the focusing point by using the shortest possible distance for propagating the waves in the propagation medium. It should be incompressible, with a Poisson's ratio greater than 0.49, and must provide low attenuation of the waves, equal to or less than 1 dB/cm. Thus, if the distance covered by the waves in the medum is 4 cm (a good distance for a portable device), attenuation will be 4 dB. Material with these characteristics may include poly-dimethyl-siloxane type silicone gel, such as Dow Corning Q7 2167 gel associated with Dow Corning Q7 2168 gel or Q7 2218 gel, or an acrylic 'sponge' type acrylic gel, or a polyacrylamide.

It should be noted that use of a liquid (as opposed to a gel) with the above characteristics as propagation medium should be avoided because of the problems of leakage or those tied to the presence of air bubbles hindering the propagation of acoustic waves because of their reflections.

Although the micropulverization device shown in the figure has only one reservoir 24 for the liquid for micropulverization, the device could have several such reservoirs containing different liquids for micropulverization and several with different characteristics, while remaining within the scope of this invention. Similarly, a micropulverization device could be designed in which the ultrasound wave generator is a broad-band transducer, so the device could be adapted to a wide range of liquids for micropulverization It should be noted that, at the end of cassette 24, the ultrasound waves generated by transducer 16 and reflected by surface 22, cross membrane 34 made of material with acoustic impedance identical or very close to that of the propagation medium in cell 12. This membrane should be made of single-component silicone elastomer shaped by compression moulding or silicone elastomer shaped by injection. Thus, attenuation of ultrasound waves can occur only inside cassette 24 when crossing the liquid for micropulverization. The ultrasound waves thus remain most effective near the focusing point, thereby eliminating the need to preheat the liquid for micropulverization. Moreover, the existence of a cell separate from the liquid for micropulverization, containing material for transmitting ultrasound waves without significant attenuation, reduces the need for a large amount of liquid for micropulverization.

It can be seen that the device according to the invention is autonomous, not bulky thanks to the smaller amount of liquid for pulverization and absence of preheating, and can thus be used as a portable device. It requires no sterilization or cleaning thanks to the permanent presence of the material for propagating ultrasound waves in the apparatus. Moreover, thanks to the easy replacement of the cassette with another, it can be used for micropulverization of various liquids. It is particularly well adapted for pneumological and otorhinolaryngological applications requiring uniform microdroplets with a diameter under 5 μm.

I claim:

1. A micropulverization device for the formation of microdroplets comprising: an ultrasound generator;

a reservoir containing a liquid to be micropulverized;

a cell for containing a propagation medium, said cell being located between said ultrasound generator and said reservoir;

means for concentrating ultrasound waves from said ultrasound generator toward a point near the surface of said liquid in said reservoir for micropulverization of said liquid;

a chamber for the formation of microdroplets; and means for diffusing said droplets;

said propagation medium having an ultrasound attenuation less than or equal to 1 dB/cm.

2. Device according to claim 10, characterized in that the reservoir (24) containing the liquid for micropulverization is located above the cell (12) containing the propagation medium with one side (34) of the reservoir made of material with about the same acoustic impedance as the propagation medium where the ultrasound waves cross said one side of the reservoir and enter the reservoir.

3. Device according to claim 1, characterized in that the reservoir (24) containing the liquid for micropulverization is a replaceable cassette.

4. Device according to claim 1 characterized in that the propagation medium is substantially incompressible, and has a Poisson's ratio greater than 0.49.

5. Device according to claim 4, characterized in that the medium for progagating ultrasound waves (13) is a silicone gel.

6. Device according to claim 1 characterized in that the ultrasound wave generator is a piezoelectric transducer.

7. Device according to claim 1 characterized in that the ultrasound wave generator (16) is a broad-band transducer so the device can be adapted for a wide range of liquids for micropulverization.

8. Device according to claim 1 further including a power supply capable of running on batteries.

* * * * *